(12) United States Patent  (10) Patent No.: US 9,327,089 B2
Jafari et al.  (45) Date of Patent: May 3, 2016

(54) METHODS AND SYSTEMS FOR COMPENSATION OF TUBING RELATED LOSS EFFECTS

(75) Inventors: Mehdi M. Jafari, Laguna Hills, CA (US); Rhomere S. Jimenez, Chula Vista, CA (US); Jeffrey K. Aviano, Escondido, CA (US)

(73) Assignee: Covidien LP, Mansfield, MA (US)

( * ) Notice: Subject to any disclaimer, the term of this patent is extended or adjusted under 35 U.S.C. 154(b) by 961 days.

(21) Appl. No.: 13/435,717

(22) Filed: Mar. 30, 2012

(65) Prior Publication Data

US 2013/0255682 A1  Oct. 3, 2013

(51) Int. Cl.
*A61M 16/00* (2006.01)

(52) U.S. Cl.
CPC ... *A61M 16/0051* (2013.01); *A61M 2016/0027* (2013.01); *A61M 2016/0033* (2013.01); *A61M 2205/702* (2013.01); *A61M 2230/46* (2013.01)

(58) Field of Classification Search
CPC ............ A61M 16/00; A61M 16/0051; A61M 2016/0027; A61M 2016/0036; A61M 2016/0039; A61M 2016/0042; A61M 2230/46; A61M 2016/0033; A61M 2205/702; A61B 5/08; A61B 5/082; A61B 5/087–5/0878
USPC ............ 128/203.14, 204.18, 204.21, 204.22, 128/204.23; 600/529, 538, 539, 540
See application file for complete search history.

(56) References Cited

U.S. PATENT DOCUMENTS

| | | | |
|---|---|---|---|
| 4,752,089 A | 6/1988 | Carter | |
| 4,921,642 A | 5/1990 | LaTorraca | |
| 4,954,799 A | 9/1990 | Kumar | |
| 5,057,822 A | 10/1991 | Hoffman | |
| 5,072,737 A | 12/1991 | Goulding | |
| 5,148,802 A | 9/1992 | Sanders et al. | |
| 5,150,291 A | 9/1992 | Cummings et al. | |
| 5,161,525 A | 11/1992 | Kimm et al. | |
| 5,237,987 A | 8/1993 | Anderson et al. | |
| 5,271,389 A | 12/1993 | Isaza et al. | |
| 5,279,549 A | 1/1994 | Ranford | |

(Continued)

OTHER PUBLICATIONS

7200 Series Ventilator, Options, and Accessories: Operator's Manual. Nellcor Puritan Bennett, Part No. 22300 A, Sep. 1990, pp. 1-196.

(Continued)

*Primary Examiner* — Jason Flick
*Assistant Examiner* — Elliot S Ruddie
(74) *Attorney, Agent, or Firm* — Merchant & Gould P.C.

(57) ABSTRACT

A method for ventilating a patient with a ventilator includes consecutively delivering a plurality of substantially equal volume amounts into a closed ventilator circuit during a ventilator self-test, receiving a pressure measurement for each volume delivery, calculating a change in pressure for each volume delivery, consecutively releasing a plurality of substantially equal volume amounts from the closed ventilator circuit during the ventilator self-test, calculating a change in pressure for each volume release, fitting the calculated change in pressure data for volume delivery and volume release to an inhalation non-linear model equation and an exhalation non-linear model equation, respectively, deriving one or more inhalation tubing compliance compensation coefficients from the inhalation non-linear model equation, and deriving one or more exhalation tubing compliance compensation coefficients from the exhalation non-linear model equation.

8 Claims, 3 Drawing Sheets

(56) References Cited

U.S. PATENT DOCUMENTS

| | | |
|---|---|---|
| 5,299,568 A | 4/1994 | Forare et al. |
| 5,301,921 A | 4/1994 | Kumar |
| 5,319,540 A | 6/1994 | Isaza et al. |
| 5,325,861 A | 7/1994 | Goulding |
| 5,333,606 A | 8/1994 | Schneider et al. |
| 5,335,654 A | 8/1994 | Rapoport |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,433,193 A | 7/1995 | Sanders et al. |
| 5,438,980 A | 8/1995 | Phillips |
| 5,443,075 A | 8/1995 | Holscher |
| 5,490,502 A | 2/1996 | Rapoport et al. |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,542,415 A | 8/1996 | Brody |
| 5,544,674 A | 8/1996 | Kelly |
| 5,546,935 A | 8/1996 | Champeau |
| 5,549,106 A | 8/1996 | Gruenke et al. |
| 5,582,163 A | 12/1996 | Bonassa |
| 5,596,984 A | 1/1997 | O'Mahony et al. |
| 5,606,968 A | 3/1997 | Mang |
| 5,630,411 A | 5/1997 | Holscher |
| 5,632,270 A | 5/1997 | O'Mahony et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,692,497 A | 12/1997 | Schnitzer et al. |
| 5,715,812 A | 2/1998 | Deighan et al. |
| 5,752,921 A | 5/1998 | Orr |
| 5,762,480 A | 6/1998 | Adahan |
| 5,771,884 A | 6/1998 | Yarnall et al. |
| 5,791,339 A | 8/1998 | Winter |
| 5,794,986 A | 8/1998 | Gansel et al. |
| 5,803,066 A | 9/1998 | Rapoport et al. |
| 5,813,399 A | 9/1998 | Isaza et al. |
| 5,826,575 A | 10/1998 | Lall |
| 5,829,441 A | 11/1998 | Kidd et al. |
| 5,845,636 A | 12/1998 | Gruenke et al. |
| 5,864,938 A | 2/1999 | Gansel et al. |
| 5,865,168 A | 2/1999 | Isaza |
| 5,881,717 A | 3/1999 | Isaza |
| 5,881,723 A | 3/1999 | Wallace et al. |
| 5,884,623 A | 3/1999 | Winter |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,934,274 A | 8/1999 | Merrick et al. |
| 6,015,388 A | 1/2000 | Sackner et al. |
| 6,017,315 A | 1/2000 | Starr et al. |
| 6,024,089 A | 2/2000 | Wallace et al. |
| 6,041,780 A | 3/2000 | Richard et al. |
| 6,047,860 A | 4/2000 | Sanders |
| 6,076,523 A | 6/2000 | Jones et al. |
| 6,095,140 A | 8/2000 | Poon et al. |
| 6,116,240 A | 9/2000 | Merrick et al. |
| 6,116,464 A | 9/2000 | Sanders |
| 6,123,073 A | 9/2000 | Schlawin et al. |
| 6,131,571 A | 10/2000 | Lampotang et al. |
| 6,135,106 A | 10/2000 | Dirks et al. |
| 6,142,150 A | 11/2000 | O'Mahoney |
| 6,148,814 A | 11/2000 | Clemmer et al. |
| 6,161,539 A | 12/2000 | Winter |
| 6,220,245 B1 | 4/2001 | Takabayashi et al. |
| 6,230,708 B1 | 5/2001 | Radko |
| 6,237,592 B1 | 5/2001 | Surjadi et al. |
| 6,240,920 B1 | 6/2001 | Strom |
| 6,269,812 B1 | 8/2001 | Wallace et al. |
| 6,273,088 B1 | 8/2001 | Hillsman |
| 6,273,444 B1 | 8/2001 | Power |
| 6,283,119 B1 | 9/2001 | Bourdon |
| 6,305,373 B1 | 10/2001 | Wallace et al. |
| 6,321,748 B1 | 11/2001 | O'Mahoney |
| 6,325,785 B1 | 12/2001 | Babkes et al. |
| 6,357,438 B1 | 3/2002 | Hansen |
| 6,360,745 B1 | 3/2002 | Wallace et al. |
| 6,369,838 B1 | 4/2002 | Wallace et al. |
| 6,371,113 B1 | 4/2002 | Tobia et al. |
| 6,390,091 B1 | 5/2002 | Banner et al. |
| 6,412,483 B1 | 7/2002 | Jones et al. |
| 6,431,171 B1 | 8/2002 | Burton |
| 6,439,229 B1 | 8/2002 | Du et al. |
| 6,450,164 B1 | 9/2002 | Banner et al. |
| 6,457,472 B1 | 10/2002 | Schwartz et al. |
| 6,467,478 B1 | 10/2002 | Merrick et al. |
| 6,488,634 B1 | 12/2002 | Rapoport et al. |
| 6,546,930 B1 | 4/2003 | Emerson et al. |
| 6,553,991 B1 | 4/2003 | Isaza |
| 6,557,553 B1 | 5/2003 | Borrello |
| 6,571,795 B2 | 6/2003 | Bourdon |
| 6,571,796 B2 | 6/2003 | Banner et al. |
| 6,588,422 B1 | 7/2003 | Berthon-Jones et al. |
| 6,622,726 B1 | 9/2003 | Du |
| 6,644,310 B1 | 11/2003 | Delache et al. |
| 6,668,824 B1 | 12/2003 | Isaza et al. |
| 6,675,801 B2 | 1/2004 | Wallace et al. |
| 6,688,307 B2 | 2/2004 | Berthon-Jones |
| 6,718,974 B1 | 4/2004 | Moberg |
| 6,725,447 B1 | 4/2004 | Gilman et al. |
| 6,739,337 B2 | 5/2004 | Isaza |
| 6,755,193 B2 | 6/2004 | Berthon-Jones et al. |
| 6,761,167 B1 | 7/2004 | Nadjafizadeh et al. |
| 6,761,168 B1 | 7/2004 | Nadjafizadeh et al. |
| 6,789,539 B2 | 9/2004 | Martinez |
| 6,796,305 B1 | 9/2004 | Banner et al. |
| 6,810,876 B2 | 11/2004 | Berthon-Jones |
| 6,814,074 B1 | 11/2004 | Nadjafizadeh et al. |
| 6,820,618 B2 | 11/2004 | Banner et al. |
| 6,837,242 B2 | 1/2005 | Younes |
| 6,866,040 B1 | 3/2005 | Bourdon |
| 6,895,964 B2 | 5/2005 | McAuliffe et al. |
| 6,915,803 B2 | 7/2005 | Berthon-Jones et al. |
| 6,921,267 B2 | 7/2005 | van Oostrom et al. |
| 6,932,084 B2 | 8/2005 | Estes et al. |
| 6,948,497 B2 | 9/2005 | Zdrojkowski et al. |
| 6,960,854 B2 | 11/2005 | Nadjafizadeh et al. |
| 6,976,487 B1 | 12/2005 | Melker et al. |
| 7,013,892 B2 | 3/2006 | Estes et al. |
| 7,036,504 B2 | 5/2006 | Wallace et al. |
| 7,040,321 B2 | 5/2006 | Göbel |
| 7,051,736 B2 | 5/2006 | Banner et al. |
| 7,077,131 B2 | 7/2006 | Hansen |
| RE39,225 E | 8/2006 | Isaza et al. |
| 7,082,945 B2 | 8/2006 | Lurie |
| 7,087,027 B2 | 8/2006 | Page |
| 7,100,607 B2 | 9/2006 | Zdrojkowski et al. |
| 7,117,438 B2 | 10/2006 | Wallace et al. |
| 7,152,598 B2 | 12/2006 | Morris et al. |
| 7,178,519 B2 | 2/2007 | Melker et al. |
| 7,270,126 B2 | 9/2007 | Wallace et al. |
| 7,270,128 B2 | 9/2007 | Berthon-Jones et al. |
| 7,367,338 B2 | 5/2008 | Baecke et al. |
| 7,369,757 B2 | 5/2008 | Farbarik |
| 7,370,650 B2 | 5/2008 | Nadjafizadeh et al. |
| 7,428,902 B2 | 9/2008 | Du et al. |

(56) References Cited

U.S. PATENT DOCUMENTS

| | | |
|---|---|---|
| 7,431,031 B2 | 10/2008 | Hete et al. |
| 7,460,959 B2 | 12/2008 | Jafari |
| 7,481,222 B2 | 1/2009 | Reissmann |
| 7,484,508 B2 | 2/2009 | Younes |
| 7,487,773 B2 | 2/2009 | Li |
| 7,527,055 B2 | 5/2009 | McAuliffe et al. |
| 7,594,508 B2 | 9/2009 | Doyle |
| 7,654,802 B2 | 2/2010 | Crawford, Jr. et al. |
| 7,694,677 B2 | 4/2010 | Tang |
| 7,717,113 B2 | 5/2010 | Andrieux |
| D618,356 S | 6/2010 | Ross |
| 7,784,461 B2 | 8/2010 | Figueiredo et al. |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| 7,901,361 B2 | 3/2011 | Rapoport et al. |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,457,706 B2 | 6/2013 | Baker, Jr. |
| 8,792,949 B2 | 7/2014 | Baker, Jr. |
| 2005/0016536 A1 | 1/2005 | Rapoport et al. |
| 2005/0039748 A1 | 2/2005 | Andrieux |
| 2005/0085799 A1 | 4/2005 | Luria et al. |
| 2005/0139212 A1 | 6/2005 | Bourdon |
| 2006/0174884 A1 | 8/2006 | Habashi |
| 2006/0249148 A1 | 11/2006 | Younes |
| 2007/0017515 A1 | 1/2007 | Wallace et al. |
| 2007/0077200 A1 | 4/2007 | Baker |
| 2007/0107728 A1 | 5/2007 | Ricciardelli et al. |
| 2007/0199566 A1 | 8/2007 | Be'eri |
| 2007/0227537 A1 | 10/2007 | Bemister et al. |
| 2007/0227538 A1 | 10/2007 | Scholler et al. |
| 2007/0272241 A1 | 11/2007 | Sanborn et al. |
| 2007/0284361 A1 | 12/2007 | Nadjafizadeh et al. |
| 2008/0023005 A1 | 1/2008 | Tokunaga |
| 2008/0053441 A1 | 3/2008 | Gottlib et al. |
| 2008/0060656 A1 | 3/2008 | Isaza |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0135044 A1 | 6/2008 | Freitag et al. |
| 2009/0007914 A1 | 1/2009 | Bateman |
| 2009/0071478 A1 | 3/2009 | Kalfon |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0249549 A1 | 9/2010 | Baker, Jr. et al. |
| 2010/0282259 A1 | 11/2010 | Figueiredo et al. |
| 2010/0288283 A1* | 11/2010 | Campbell et al. ........ 128/207.14 |
| 2010/0300446 A1 | 12/2010 | Nicolazzi et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1* | 8/2011 | Jourdain et al. ............... 600/538 |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |

(56) References Cited

U.S. PATENT DOCUMENTS

| | | |
|---|---|---|
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0304995 A1 | 12/2012 | Kauc |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0025596 A1 | 1/2013 | Jafari et al. |
| 2013/0025597 A1 | 1/2013 | Doyle et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0167842 A1* | 7/2013 | Jafari et al. .............. 128/204.21 |
| 2013/0167843 A1 | 7/2013 | Kimm et al. |
| 2013/0192599 A1 | 8/2013 | Nakai et al. |
| 2013/0220324 A1 | 8/2013 | Jafari et al. |
| 2013/0233314 A1* | 9/2013 | Jafari et al. .............. 128/204.23 |
| 2013/0255685 A1 | 10/2013 | Jafari et al. |
| 2014/0331998 A1* | 11/2014 | Berthon-Jones ......... 128/202.22 |

OTHER PUBLICATIONS

7200 Ventilatory System: Addendum/Errata. Nellcor Puritan Bennett, Part No. 4-023576-00, Rev. A, Apr. 1988, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

\* cited by examiner

METHODS AND SYSTEMS FOR COMPENSATION OF TUBING RELATED LOSS EFFECTS

Medical ventilator systems have long been used to provide ventilatory and supplemental oxygen support to patients. These ventilators typically comprise a source of pressurized oxygen which is fluidly connected to the patient through a conduit or tubing. Further, ventilators often measure and calculate various ventilator and/or patient parameters during the ventilation of a patient. For example, spirometry is a major feature with significant clinical utility. Spirometry data provides valuable information for patient evaluation and clinical decision making. Collecting accurate spirometry data relies in part on collecting accurate circuit compliance data. In order to deliver an accurate set tidal volume to a patient in a respiratory ventilation system, circuit compliance should be compensated. Without compensation for the circuit compliance, inaccurate volume delivery and inadequate flow will be delivered to the patient. Therefore, various designs and algorithms have been proposed to facilitate the circuit compliance compensation in the respiratory ventilation system. In some instances, algorithms that directly add an estimate of patient circuit volume to a set tidal volume are used. An estimate of patient circuit volume is added to a set tidal volume by increasing the volume target, which ultimately increments the target peak airway pressure. The patient circuit volume is computed using the average peak airway pressure of previous mandatory breaths and an estimate of the patient circuit compliance, the patient circuit volume is thus continuously elevated breath after breath. Currently, the settings or approaches in many of the circuit compliance compensation designs or algorithms cannot achieve precise volume delivery. The burden of achieving accurate volume delivery is then generally left for the clinician.

Accordingly, accurate compensation of circuit loss effects is an important performance characteristic of ventilators. Loss effect-compensated ventilation aims to ensure optimum spirometry data in a variety of circuit configurations.

This disclosure describes systems and methods for providing loss effect compensation during ventilation of a patient to optimize accuracy of estimated exhaled and inhaled tidal volumes. Further, this disclosure describes systems and methods for providing patient lung compliance estimates and circuit resistance estimates based on loss effect calculations.

According to embodiments, a method is provided for ventilating a patient with a ventilator. The method comprises: consecutively delivering a plurality of substantially equal volume amounts into a closed ventilator circuit during a ventilator self-test; receiving a pressure measurement for each volume delivery; calculating a change in pressure for each volume delivery; consecutively releasing a plurality of substantially equal volume amounts from the closed ventilator circuit during the ventilator self-test; calculating a change in pressure for each volume release; fitting the calculated change in pressure data for volume delivery and volume release to an inhalation non-linear model equation and an exhalation non-linear model equation, respectively; deriving one or more inhalation tubing compliance compensation coefficients from the inhalation non-linear model equation; and deriving one or more exhalation tubing compliance compensation coefficients from the exhalation non-linear model equation.

According to further embodiments, a ventilator system is provided. The ventilator system comprises: a pressure generating system adapted to generate a volume of breathing gas; a ventilation tubing system including a patient interface for connecting the pressure generating system to a patient; at least one sensor operatively coupled to at least one of the pressure generating system and the ventilation tubing system; a loss effect compensation module, the loss effect compensation module configured to provide at least one instruction to consecutively deliver a plurality of substantially equal volume amounts into a closed ventilator circuit during a ventilator self-test, receive a pressure measurement for each volume delivery, calculate a change in pressure for each volume delivery, consecutively release a plurality of substantially equal volume amounts from the closed ventilator circuit during the ventilator self-test, calculate a change in pressure for each volume release, fit the calculated change in pressure data for volume delivery and volume release to an inhalation non-linear tubing compliance model equation and an exhalation non-linear tubing compliance model equation, respectively, derive one or more inhalation tubing compliance compensation coefficients from the inhalation non-linear model equation, and derive one or more exhalation tubing compliance compensation coefficients from the exhalation non-linear model equation; and a processor in communication with the pressure generating system, the at least one sensor, and the loss effect compensation module and configured to receive the at least one instruction to consecutively deliver a plurality of substantially equal volume amounts from the loss effect compensation module.

According to further embodiments, a computer-readable medium having computer-executable instructions for performing a method of ventilating a patient with a ventilator is provided. The method comprises: consecutively delivering a plurality of substantially equal volume amounts into a closed ventilator circuit during a ventilator self-test; receiving a pressure measurement for each volume delivery; calculating a change in pressure for each volume delivery; consecutively releasing a plurality of substantially equal volume amounts from the closed ventilator circuit during the ventilator self-test; calculating a change in pressure for each volume release; fitting the calculated change in pressure data for volume delivery and volume release to an inhalation non-linear compliance model equation and an exhalation non-linear compliance model equation, respectively; deriving one or more inhalation tubing compliance compensation coefficients from the inhalation non-linear model equation; and deriving one or more exhalation tubing compliance compensation coefficients from the exhalation non-linear model equation.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiments of systems and methods described below and are not meant to limit the scope of the invention in any manner, which scope shall be based on the claims appended hereto.

DETAILED DESCRIPTION

Figure 1:
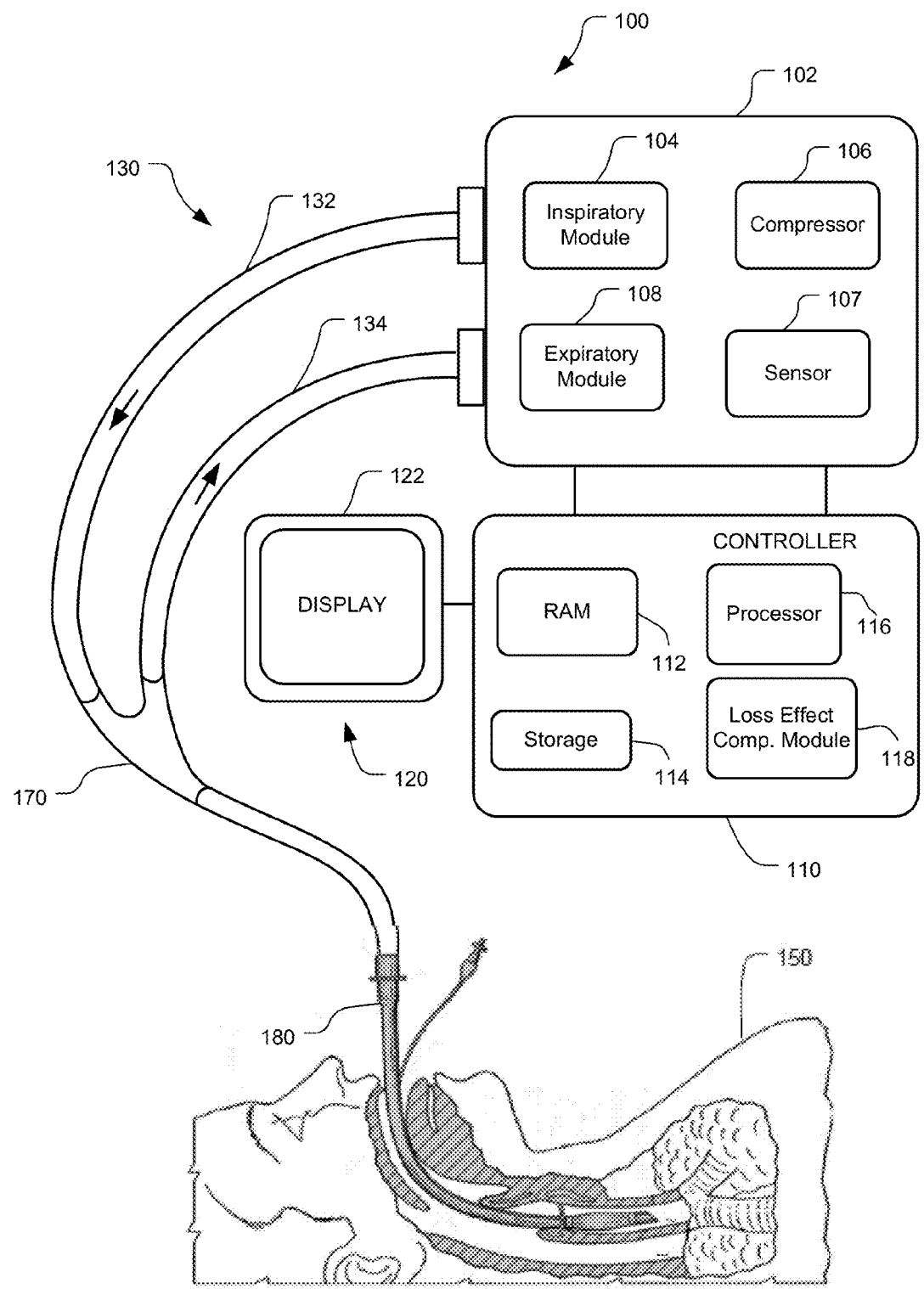
FIG. 1 illustrates an embodiment of a ventilator.

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

Spirometry data provides valuable information for patient evaluation and clinical decision making. Accordingly, the accuracy of the spirometry data is an important performance characteristic of ventilators. Spirometry volumes may be calculated by integrating the net flow, which is a linear combination of flow rates measured by a number of flow sensors at both the inspiratory (delivery) side and at the exhalation (exhaust) side. These flow sensors possess different uncertainties and the overall accuracy performance is a function of a combination of the properties of individual devices. Exhaled tidal volume is measured during the expiratory phase of a ventilator breath while a base flow is delivered through the patient circuit. To determine the volume of gas inhaled or exhaled by the patient, the net flow (total delivered flow minus total flow through exhalation module) is used for integration. That is, the delivered base flow is subtracted from the sum of the base flow and patient flow exiting through the exhalation port. Delivered flow during exhalation is base flow and consists of a desired combination of appropriate gases. The flow exiting the exhalation module during the active phase of patient exhalation is the sum of base flow delivered by the ventilator and exhaled flow from the patient's lung. The flow entering the patient's lung during inhalation is the algebraic sum of the total delivered flow minus the flow compressed in the tubing and any flow exiting through the exhalation module. According to embodiments, it is important to account for the volume of gas remaining in the circuit for both inhalation and exhalation spirometry. The spirometry parameter of exhaled tidal volume is measured during patient's active exhalation. Therefore, the smaller the ventilator-delivered base flow is during active exhalation, the smaller the uncertainty contributed by measuring the same quantity by different sensors (once on the delivery side and a second time as a portion of exhaust gas on the exhalation side). Accounting for circuit compliance is particularly critical under neonatal conditions, where tidal volumes and exhaled flow rates are relatively smaller and may be some orders of magnitude smaller than a base flow.

Accordingly, the systems and methods described herein provide ventilation with loss effect compensation to optimize the accuracy of estimated inhaled and exhaled tidal volume.

FIG. 1 is a diagram illustrating an embodiment of an exemplary ventilator 100 connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130) may be a two-limb (shown) or a one-limb circuit for carrying gases to and from the patient 150. In a two-limb embodiment, a fitting, typically referred to as a "wye-fitting" 170, may be provided to couple a patient interface 180 (as shown, an endotracheal tube) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 and the expiratory module 108 to provide a gas source for ventilatory support via inspiratory limb 132.

The inspiratory module 104 is configured to deliver gases to the patient 150 according to prescribed ventilatory settings. In some embodiments, inspiratory module 104 is configured to provide ventilation according to various breath types.

The expiratory module 108 is configured to release gases from the patient's lungs according to prescribed ventilatory settings. The expiratory module 108 is associated with and/or controls an expiratory valve for releasing gases from the patient 150. Further, the expiratory module 108 may instruct the pressure generating system 102 and/or the inspiratory module 104 to deliver a base flow during exhalation.

The ventilator 100 may also include one or more sensors 107 communicatively coupled to ventilator 100. The sensors 107 may be located in the pneumatic system 102, ventilation tubing system 130, and/or on the patient 150. The embodiment of FIG. 1 illustrates a sensor 107 in pneumatic system 102.

Sensors 107 may communicate with various components of ventilator 100, e.g., pneumatic system 102, other sensors 107, expiratory module 108, inspiratory module 104, processor 116, controller 110, and loss effect compensation module 118 (illustrated as "Loss Effect Comp. Module"), and any other suitable components and/or modules. In one embodiment, sensors 107 generate output and send this output to pneumatic system 102, other sensors 107, expiratory module 108, inspiratory module 104, processor 116, controller 110, loss effect compensation module 118, and any other suitable components and/or modules.

Sensors 107 may employ any suitable sensory or derivative technique for monitoring one or more patient parameters or ventilator parameters associated with the ventilation of a patient 150. Sensors 107 may detect changes in patient parameters indicative of patient inspiratory or expiratory triggering, for example. Sensors 107 may be placed in any suitable location, e.g., within the ventilatory circuitry or other devices communicatively coupled to the ventilator 100. Further, sensors 107 may be placed in any suitable internal location, such as, within the ventilatory circuitry or within components or modules of ventilator 100. For example, sensors 107 may be coupled to the inspiratory and/or expiratory modules for detecting changes in, for example, circuit pressure and/or flow. In other examples, sensors 107 may be affixed to the ventilatory tubing or may be embedded in the tubing itself. According to some embodiments, sensors 107 may be provided at or near the lungs (or diaphragm) for detecting a pressure in the lungs. Additionally or alternatively, sensors 107 may be affixed or embedded in or near wye-fitting 170 and/or patient interface 180. Indeed, any sensory device useful for monitoring changes in measurable parameters during ventilatory treatment may be employed in accordance with embodiments described herein.

As should be appreciated, ventilatory parameters are highly interrelated and, according to embodiments, may be either directly or indirectly monitored. That is, parameters may be directly monitored by one or more sensors 107, as described above, or may be indirectly monitored or estimated by derivation according to the Equation of Motion (as discussed in more detail, infra) or other known relationships.

The pneumatic system 102 may include a variety of other components, including mixing modules, valves, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.).

In one embodiment, the operator interface 120 of the ventilator 100 includes a display 122 communicatively coupled to ventilator 100. Display 122 provides various input screens, for receiving clinician input, and various display screens, for presenting useful information to the clinician. In one embodiment, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122.

Display 122 may also provide useful information in the form of various ventilatory data regarding the physical condition of a patient 150. The useful information may be derived by the ventilator 100, based on data collected by a processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100. In some embodiments, the display 122 may illustrate a minimum exhalation flow, a minimum exhalation time, a maximum exhalation time, a desired base flow, a desired inspiratory trigger, an inspiratory trigger, a base flow, an exhalation flow, an estimated loss effect volume, an exhalation pressure, and/or any other information known, received, or stored by the ventilator 100.

In some embodiments, controller 110 includes memory 112, one or more processors 116, storage 114, and/or other components of the type commonly found in command and control computing devices. Controller 110 may further include a loss effect compensation module 118 as illustrated in FIG. 1. In alternative embodiments, the loss effect compensation module 118 may be located in other components of the ventilator 100, such as in the pressure generating system 102 (also known as the pneumatic system 102).

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

The loss effect compensation module 118 may provide improved compensation for tubing compliance loss effects. A loss effect may be a dynamic effect on a ventilator tubing system due to volume contraction and expansion during inspiration and exhalation (e.g., kinetic energy, convective acceleration effects, etc.). Hereinafter, a ventilator tubing system may also be referred to as a "circuit" or "patient circuit". Compliance may generally be defined as a relative ease with which something distends. Tubing compliance volume may be defined as the differential volume that is delivered into and remains in the circuit and causes a change of pressure in the circuit. In some embodiments, compliance may be determined by the equation:

$$V_{comp} = C_{tubing} * (\Delta P)$$

Where $V_{comp}$=tubing compliance volume, $C_{tubing}$=tubing compliance, $\Delta P$=end inspiratory pressure $P_{iend}$ minus end expiratory pressure $P_{eend}$.

Typical tubing compliance measurements utilize a constant for $C_{tubing}$ when determining a tubing compliance volume (i.e., the volume compressed in the circuit due to the pressure change). However, in most ventilator systems, one or more loss effect parameters may affect tubing compliance volumes as well and such loss effects are not addressed by the above equation. By utilizing a non-linear loss effect model, volume compensation that accounts for loss effects during delivery and spirometry may provide improved delivery and spirometry performance.

The loss effect compensation module 118 may be configured to instruct the ventilator, during a ventilator self-test, to deliver a plurality of volume amounts into a closed ventilator circuit or to release a plurality of volume amounts from the circuit. In a closed ventilator circuit, a patient wye (e.g., patient wye 170) may be blocked or substantially blocked.

During a delivery self-test portion, one or more ventilator components (e.g., inspiratory module 104) may receive instructions to fill at least a portion of the circuit (e.g., inspiratory limb 132 or expiratory limb 134) with a volume of gas. Delivery may be repeated. The number of and spacing between consecutive volume deliveries may be pre-determined by the ventilator or by an operator. For instance, volume deliveries may be substantially equal volume amounts and may be delivered over a specified time duration. Volume deliveries may also be delivered in substantially equal time increments (e.g., the ventilator may add 5 or 15 or 100 mL of gas to the circuit every second for one second).

The loss effect compensation module 118 may also, after reaching a predetermined end point, reduce the pressure in the tubing by incrementally releasing fixed amounts of volume in a controlled manner similar to the way it increased pressure as described above. This allows data to be obtained for the loss effect during a reduction of pressure, which may be different than the loss effect observed during pressurization.

The loss effect compensation module 118 may then receive pressure information for each volume delivery and release. Adding a known volume to the closed or substantially closed circuit may generally result in a pressure increase. Subtracting a known volume from the closed or substantially closed circuit may generally result in a pressure decrease. However, each consecutively delivered volume, while substantially constant, may result in a slightly different pressure increase (e.g., each pressure increase may be less than the previous pressure increase even when the volumes added are the same). That is, additional volume deliveries may not generate equal amounts of pressure on one or more ventilator components. Such pressure increases within the tubing system may be measured by at least one component of the ventilator (e.g., sensor 107). Likewise, each consecutively released volume, while substantially constant, may result in a slightly different pressure decrease (e.g., each pressure decrease may be less than the previous pressure decrease even when the volumes released are the same). That is, additional volume releases may not release equal amounts of pressure on one or more ventilator components.

In some embodiments, a sensor may measure a pressure after each volume delivery to and/or release from the closed circuit. The sensor may be configured to measure a pressure amount at the patient wye or elsewhere in the circuit. The sensor may be any suitable sensing device as known by a person of skill in the art for a ventilator. The sensor may then transfer the pressure data to another component of the ventilator 100, such as controller 110, processor 116, and/or loss effect compensation module 118. In embodiments where the sensor transfers the pressure data to a component other than the loss effect compensation module 118, the loss effect compensation module 118 may receive the pressure information from the other component of the ventilator. Pressure data may be collected to derive applicable values for the parameters of the best fit to the data for the tubing configuration in use.

The loss effect compensation module 118 may calculate a relative change in pressure for each volume delivery and/or release based on the collected pressure data. For instance, a second pressure resulting from a second volume delivery may be subtracted from a first pressure resulting from a first volume delivery to calculate a change in pressure between the two volume deliveries. In some embodiments, change in pressure data may be stored in a memory (e.g., storage 114) for use in later calculations.

The loss effect compensation module 118 may then fit the measured change in pressure data to a non-linear curve. For instance, the loss effect compensation module 118 may plot the change in pressure data to derive a curve from the data. In some embodiments, one or more other components of ventilator 100 (e.g., processor 116) may be further configured to plot calculated pressure change data. Pressure change data may be graphically plotted via any suitable means. For example, according to embodiments, derived compliance values for each pressure reading may be plotted versus pressure corresponding data (e.g., delivery instance), or versus any other suitable parameter as may be useful to a clinician. According to embodiments, pressure may be plotted such that each delivery instance may be independently identified. Alternatively, the unit may utilize a suitable curve-matching algorithm to fit a curve with optimum matching criterion (for example, R2 statistic) and save the parameters of the model for later use during ventilation.

The loss effect compensation module 118 may then derive tubing compliance compensation coefficients from the non-linear curve. In some embodiments, at least two compliance values may be derived from the plotted data, one for use during inhalation (using pressure changes measured during an inhalation simulation) and one for use during exhalation (using pressure changes measured during an exhalation simulation). In one embodiment, an inhalation tubing compliance compensation coefficient may be characterized by the following equation:

$$C_i = c_1 \ln(\Delta P) + c_2$$

Where $C_i$=tubing compliance for volume contraction (gas is compressed into the circuit and patient lung and pressure is raised), $c_1$ and $c_2$ are constants derived during an inhalation simulation, and $\Delta P = P_{iend} - P_{eend}$. Any change in the geometry or volume of the circuit (due to the elasticity of the tubing material) is also pressure-dependent and will be captured during the simulation.

In another embodiment, an inhalation tubing compliance compensation coefficient may be characterized by the following equation:

$$C_i = c_1 (\Delta P)^{c_2}$$

Where $C_i$=tubing compliance for volume contraction, $c_1$ and $c_2$ are constants derived during an inhalation simulation, and $\Delta P = P_{iend} - P_{eend}$.

Similar model equations may be derived from the fitted curve to estimate an exhalation tubing compliance for volume expansion compliance (respiratory gas expanding from a compressed state during inhalation to decompress into the ambient). For instance, an exhalation tubing compliance compensation coefficient may be characterized by the following equation:

$$C_e = c_1 \ln(\Delta P) + c_2$$

Where $C_e$=tubing compliance for volume expansion, $c_1$ and $c_2$ are constants derived during an exhalation simulation, and $\Delta P = P_{iend} - P_{eend}$.

In another embodiment, an exhalation tubing compliance compensation coefficient may be characterized by the following equation:

$$C_e = c_1 (\Delta P)^{c_2}$$

Where $C_e$=tubing compliance for volume expansion, $c_1$ and $c_2$ are constants derived during an exhalation simulation, and $\Delta P = P_{iend} - P_{eend}$.

Tubing compliance compensation coefficient for a circuit may be saved in a memory (e.g., storage 114) to be utilized during ventilation with that particular circuit. The model equation for estimating a tubing compliance compensation coefficient may be any suitable model providing a reasonably accurate prediction of the tubing compliance based on ventilator settings, pressure measurements, available hardware characteristics, and/or patient respiratory mechanics parameters extracted from ventilator data. Selection of a model may be optimized on a regressive basis (e.g., loss effect compensation module 118 may select the model that returns the highest $R^2$ value). The model equations described above are non-limiting examples of how an estimate may be obtained based on the measured pressure values. A tubing compliance compensation coefficient may be estimated during a self-test whenever a tubing system is modified (e.g., a tube of tubing system 130 is replaced, or tubing system 130 is replaced in its entirety).

The loss effect compensation module 118 may then estimate a tubing compliance volume of the circuit (e.g., the amount of volume that may remain in ventilation tubing system 130 during inhalation and/or exhalation). For instance, the loss effect compensation module 118 may utilize an appropriate tubing compliance compensation coefficient (either $C_i$ or $C_e$) to estimate a tubing compliance volume during either inhalation or exhalation.

Generally, tubing compliance volume may be estimated using the equation:

$$V_{comp} = C_{tubing} * (\Delta P)$$

Where $V_{comp}$=tubing compliance volume, $C_{tubing}$=$C_i$ or $C_e$, and $\Delta P = P_{iend} - P_{eend}$.

That is, during inhalation, an inhalation tubing compliance coefficient may be used in the compliance volume equation to compensate for the effect of compressed volume during inhalation. For instance, to estimate tubing compliance for volume contraction, the equation may be:

$$V_{comp} = C_i * (\Delta P)$$

Where $C_i = c_1 (\Delta P)^{c_2}$, $c_1$ and $c_2$ are constants derived during an inhalation simulation, and $\Delta P = P_{iend} - P_{eend}$ (pressure increase).

In contrast, during exhalation, an exhalation tubing compliance coefficient may be used in the compliance volume equation to compensate for the effect of expanded volume during exhalation. For instance, to estimate tubing compliance for volume expansion, the equation may be:

$$V_{comp} = C_e * (\Delta P)$$

Where $C_e = c_1 (\Delta P)^{c_2}$, $c_1$ and $c_2$ are constants derived during an exhalation simulation, and $\Delta P = P_{iend} - P_{eend}$ (pressure drop).

The volume compensation equation may be any suitable model providing a reasonably accurate estimation of the tubing compliance based on ventilator settings, pressure measurements, available hardware characteristics, and/or patient respiratory mechanics parameters extracted from ventilator data. The model described above is a non-limiting example of how a tubing compliance volume estimate may be obtained based on a tubing compliance compensation coefficient. It is further contemplated that more complex modeling strategies (building a bank of models to serve different ventilator settings and/or patient conditions) may also be utilized. Furthermore, parameters of such models may be dynamically updated and optimized during ventilation.

During ventilation, loss effect compensation module 118 may estimate a total volume delivery amount or an exhaled tidal volume. For instance, during an inhalation, loss effect compensation module 118 may estimate how much total volume to deliver to provide the desired tidal volume to the patient by adding an inhalation tubing compliance compensation volume to the desired tidal volume. After an exhalation, a total exhaled volume may be measured and loss effect compensation module 118 may subtract the estimated exhalation tubing compliance compensation volume from the total to determine how much volume was exhausted (e.g., the exhaled tidal volume) by the patient.

Alternatively, the loss effect compensation module 118 may allow the processor 116 or controller 110 to more accurately estimate inhaled and exhaled tidal volume and/or spirometry. For instance, the loss effect compensation module 118 may send the estimated tubing compliance volume to other components of the ventilator 100, such as the controller 110, processor 116, loss effect compensation module 118, pneumatic system 102, and/or display 122 for use in calculating delivery (e.g., delivery of an inhaled tidal volume) and spirometry (e.g., measurement of an exhaled tidal volume) parameters and compensating for tubing compliance volume during delivery and spirometry.

Figure 2:
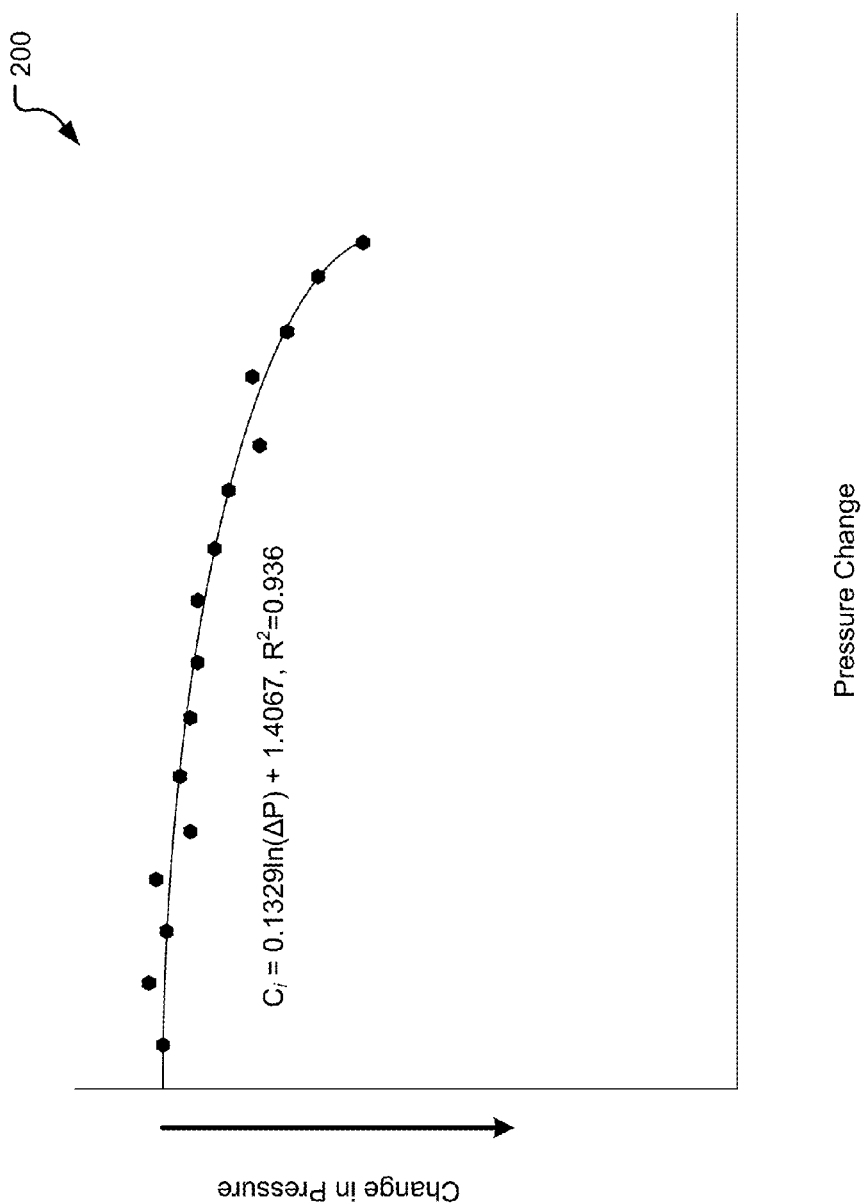
FIG. 2 illustrates an embodiment of a graph illustrating a pressure-based compensation model according to embodiments of the disclosure.

FIG. 2 illustrates an example of plotted compliance against pressure data. In the example illustrated in FIG. 2, a ventilator self-test was run on a Smoothbore® adult circuit, and pressure and volume measurements were taken. The y-axis is compliance magnitude and the x-axis is pressure change. For each pressure-volume set, a corresponding compliance value was calculated. A pressure-based model was then fitted to the derived data. A ventilator self-test was run as described above for both an inhalation and an exhalation. Two pressure-based models were derived from each of the inhalation self-test pressure data and the exhalation self-test pressure data. The models derived for $C_i$ (tubing compliance for volume contraction) and $C_e$ (tubing compliance for volume expansion) for the circuit resulted in the following coefficients:

$$C_i = 0.1329 \ln(\Delta P) + 1.4067, R^2 = 0.936$$

$$C_i = 1.4659 (\Delta P)^{0.78}, R^2 = 0.933$$

$$C_e = 0.0251 \ln(\Delta P) + 0.9621, R^2 = 0.9508$$

$$C_e = 1.0049 (\Delta P)^{0.721} + 0.9621', R^2 = 0.9645$$

Where $C_i$=tubing compliance for volume contraction, $C_e$=tubing compliance for volume expansion, and $\Delta P = P_{iend} - P_{eend}$. FIG. 2 illustrates the data plotted to derive the model $0.1329 \ln(\Delta P) + 1.4067$, which yielded the highest $R^2$ value for the collected data. As described above, the model resulting in the highest $R^2$ value (e.g., the exponential model for both $C_i$ and $C_e$ may be selected for input into the loss effect adjusted compliance volume equation:

$$V_{comp} = C_{tubing} * (P_{iend} - P_{eend})$$

Where $V_{comp}$=tubing compliance volume, $C_{tubing}$=$C_i$ or $C_e$, $P_{iend}$=end inspiratory pressure, and $P_{eend}$=end expiratory pressure. This exemplary embodiment is not meant to be limiting. Additional, algorithms may cover different types of breathing behavior and ventilator settings as well as estimate of ventilator parameters. Multiple model parameters and more involved optimization strategies can be utilized as suitable for application needs.

In further embodiments, tubing compliance volume may be utilized to more accurately estimate respiratory resistance during inhalation and exhalation. Respiratory resistance refers to frictional forces that resist airflow, e.g., due to synthetic structures (e.g., endotracheal tube, expiratory valve, etc.), anatomical structures (e.g., bronchial tree, esophagus, etc.), or viscous tissues of the lungs and adjacent organs. Respiratory resistance may be interchangeably referred to herein as resistance. Resistance is highly dependent on the diameter of the airway. That is, a larger airway diameter entails less resistance and a higher concomitant flow under the same pressure gradient. Alternatively, for the same pressure gradient, a smaller airway diameter entails higher resistance and a lower concomitant flow. In fact, decreasing the diameter of the airway results in an exponential increase in resistance (e.g., two-times reduction of diameter increases resistance by sixteen times).

By way of general overview, the basic elements impacting ventilation may be described by the following ventilatory equation (also known as the Equation of Motion):

$$P_m + P_v = V_T/C + R^*F$$

Here, $P_m$ is a measure of muscular effort that is equivalent to the pressure generated by the respiratory muscles of a patient. During inspiration, $P_v$ represents the positive airway pressure delivered by a ventilator (generally in cm $H_2O$). $V_T$ represents the tidal volume delivered based on the pressure supplied, C refers to the respiratory compliance, R represents the respiratory resistance, and F represents the gas flow during inspiration (generally in liters per minute (L/m)). A more accurate estimation of delivered tidal volume $V_T$ may be derived by using the pressure-based model including an estimate of tubing compliance for volume contraction $C_i$ (e.g., tubing compliance during inhalation) estimated via the embodiments described above.

Alternatively, during exhalation, the Equation of Motion may be represented as:

$$P_a + P_t = V_{TE}/C + R^*F$$

Here, $P_a$ represents the positive pressure existing in the lungs (generally in cm $H_2O$), $P_t$ represents the transairway pressure, $V_{TE}$ represents the tidal volume exhaled, C refers to the respiratory compliance, R represents the respiratory resistance, and F represents the gas flow during exhalation (generally in liters per minute (L/m)). Thus, a more accurate estimation of exhaled tidal volume $V_{TE}$ may be derived by using the pressure-based model deriving an estimate of tubing compliance for volume expansion $C_e$ (e.g., tubing compliance during exhalation) estimated via the embodiments described above.

In further embodiments, tubing compliance volume may be utilized to estimate patient lung compliance. As related to ventilation, lung compliance refers to the lung volume achieved for a given amount of delivered pressure ($C=\Delta V/\Delta P$). One or more components of the ventilator (e.g., processor 116) may be configured to utilize the estimated delivered volume, based on the tubing compliance calculation, to estimate lung volume compliance.

Figure 3:
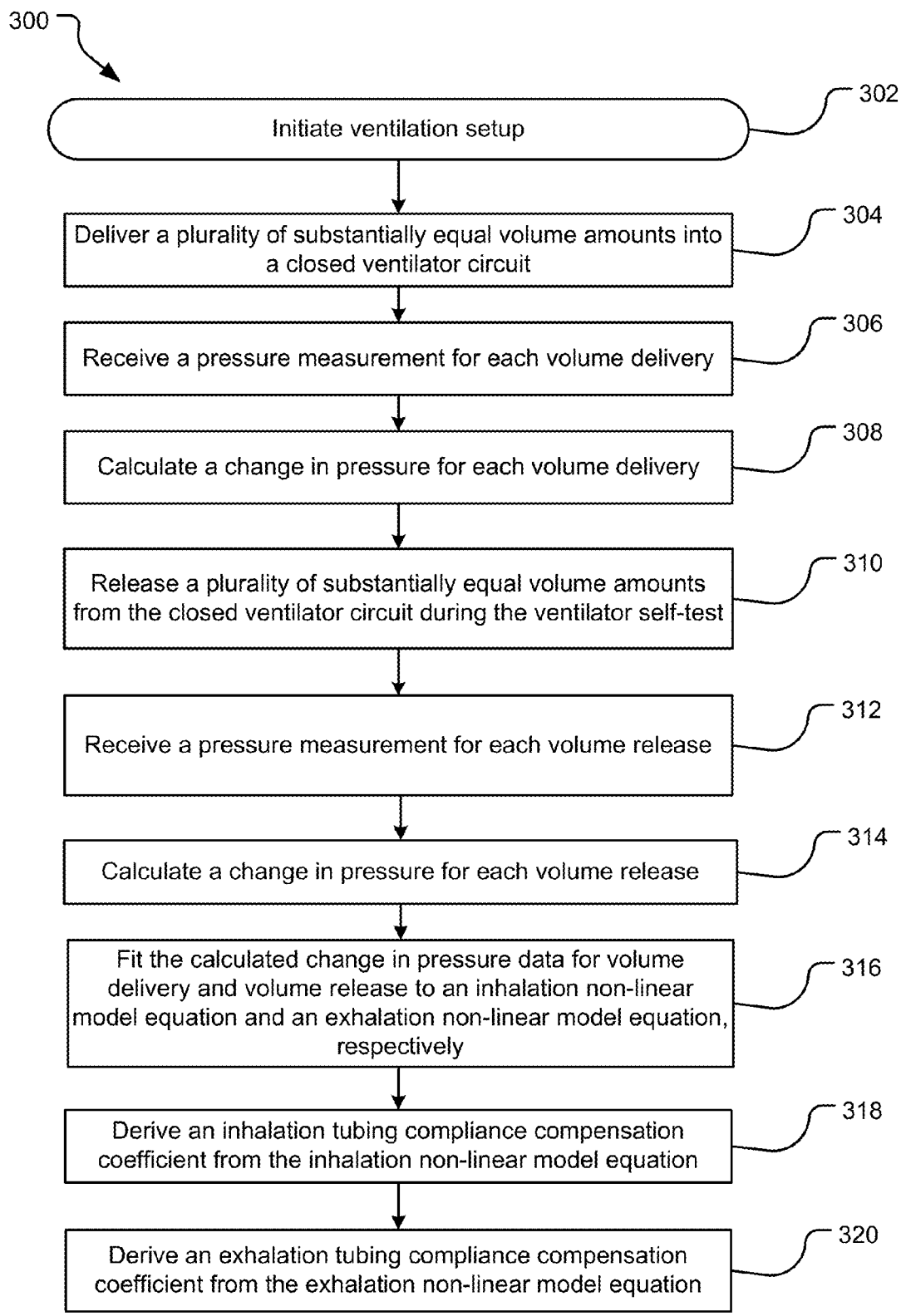
FIG. 3 illustrates an embodiment of a method for deriving patient circuit compliance during ventilator setup Self-Test prior to starting ventilating a patient on a ventilator.

FIG. 3 is a flow chart illustrating an embodiment of a method 300 for compensating for tubing compliance loss effects.

Method 300 may begin during ventilation setup. For instance, during setup the ventilator may receive one or more input parameters from a user. The ventilator may also run one or more self-tests relating to one or more ventilator components. During self-test, one or more ventilator components may be configured to measure the amount of volume that is delivered out of the ventilator and the amount that is returned. The volume that is delivered out of the ventilator to the patient circuit may represent a volume to be delivered into the patient's lung. Ultimately, as will be discussed below, the volume in the lung may be estimated by subtracting the change in volume in the patient circuit (compliance volume) as a result of the gas volume given to the patient circuit-patient system from the delivered volume. Because the volume in the patient circuit is calculated based on the pressure change during the inspiratory phase, it is important to obtain an accurate pressure measurement. However, during inspiration, heat is generated by the compressed gas which in turn increases the pressure inside the patient circuit. This phenomenon, called adiabatic compression, will bias the pressure measurement which, if not accounted for, will produce inaccurate calculations of the volume in the patient circuit. Also, gas flow will produce pressure drops across the patient circuit which, again, will affect the calculations of the volume in the patient circuit. According to embodiments, during a circuit (e.g., tubing) self-test, a plurality of volume amounts may be delivered to the patient circuit. Volume amounts may be delivered into the circuit prior to connection of the ventilator to a patient. Pressure values for each volume delivery may be detected and recorded. According to further embodiments, delivery of a set volume into the closed ventilation circuit may be repeated several times, and additional pressure data is collected. Pressure differential data and derived compliance values may then be fitted to at least one non-linear model equation. A tubing compliance compensation coefficient may be derived from the equation, and the tubing compliance compensation may then be utilized in a loss effect volume compensation equation during patient ventilation to accurately compensate for loss effects due to tubing compliance.

As illustrated, method 300 includes an initiate self-test operation 302. According to embodiments, a ventilator (e.g., ventilator 100) may receive an indication that a self-test has been initiated. Self-test may be triggered by an operator, may be pre-scheduled, or may begin spontaneously based on one or more ventilator settings.

After initiate self-test operation 302, method 300 may proceed to delivery operation 304 during the self-test (or alternatively, later, during patient ventilation, using the derived coefficients described above to compensate for circuit compliance). The loss effect compensation module 118 may be configured to instruct the ventilator, during a ventilator self-test, to deliver a plurality of volume amounts into a closed ventilator circuit. In a closed ventilator circuit, a patient wye (e.g., patient wye 170) may be blocked or substantially blocked. In some embodiments, at least one component of the ventilator may deliver a plurality of volume amounts to the circuit during a delivery operation 304. For instance, during a self-test, a plurality of volume amounts may be delivered into a circuit prior to connection of the circuit to a patient. One or more ventilator components (e.g., inspiratory module 104) may receive instructions from loss compensation module 118 to fill at least a portion of the circuit (e.g., inspiratory limb 132 or expiratory limb 134) with a volume of gas. According to embodiments, the ventilator may deliver an initial volume amount to the circuit. Prior to the initial delivery, the circuit may or may not be pressurized. The initial volume amount and the subsequent plurality of volume amounts may be delivered into the circuit prior to connection of the circuit to a patient (e.g., patient 150). Further, a ventilator wye (e.g., wye-fitting 170) may be closed such that the ventilator circuit may be substantially closed. According to embodiments, the plurality of volume amounts may be predetermined by the ventilator based on the configuration of the ventilator or determined by the ventilator based on ventilator and/or patient parameters or settings. In an alternative embodiment, the initial volume amount may be input or selected by an operator. For instance, according to embodiments, an initial volume amount value is received via input or selection by an operator, e.g., via a graphical user interface, keyboard, mouse, and/or any other suitable input device for receiving and interpreting operator commands, instructions, and/or selections. In an alternative embodiment, the desired volume is determined by the ventilator. Volume delivery during self-test may be repeated. During subsequent deliveries, the ventilator may repeatedly deliver a volume amount (e.g., substantially equal to the first delivered volume amount) into the closed circuit. The number of and spacing between volume deliveries may be pre-determined by the ventilator or by an operator. For instance, volume deliveries may be delivered over a specified time duration. Volume deliveries may also be delivered in substantially equal time increments.

At receive operation 306, one or more pressure measurements may be received. According to some embodiments, a pressure measurement for each volume delivery may be received. Adding an amount of volume to the closed or substantially closed circuit may generally result in a pressure increase. However, each consecutively delivered volume amount, while substantially constant, may result in a slightly different pressure increase (e.g., each pressure increase may be less than the previous pressure increase). That is, additional volume deliveries may not exert equal amounts of pressure on one or more ventilator components. Such pressure increases within the tubing system may be measured by at least one component of the ventilator (e.g., sensor 107). A sensor may measure the tubing pressure based on the added volume into the circuit. The tubing pressure may alternatively be measured by utilizing any known suitable methods or systems. A sensor may measure a pressure after each volume delivery. The sensor may be configured to measure a pressure amount at the patient wye or elsewhere in the circuit. The sensor may be any suitable sensing device as known by a person of skill in the art for a ventilator. The sensor may then transfer the pressure data to another component of the ventilator 100, such as controller 110, processor 116, and/or loss effect compensation module 118. In embodiments where the sensor transfers the pressure data to a component other than the loss effect compensation module 118, the loss effect compensation module 118 may receive the pressure information from the other component of the ventilator 100. Pressure data may be collected to derive applicable values for the parameters of the best fit to the data for the tubing configuration in use. Tubing pressure measurements may be sent to the loss effect compensation module 118 for further processing. Tubing pressure measurements may also be stored in a memory (e.g., storage 114).

At calculate operation 308, a change in pressure for each volume delivery may be calculated. For instance, during the change in pressure calculation operation 308, the loss effect compensation module 118 may calculate a relative change in pressure for each volume delivery. The change in tubing pressure may be based on the added volume into the tubing system after each volume delivery. In some embodiments, each subsequent volume delivery pressure may be subtracted from a previous volume delivery pressure to calculate a change in pressure between the two volume deliveries. The change in tubing pressure may be calculated by utilizing any known suitable methods or systems. In alternative embodiments, method 300 may utilize a processor (e.g., processor 116) to calculate the change in tubing pressure, and transfer the change in pressure data to the loss effect compensation module 118. Processor may include any suitable processing device as known by a person of skill in the art for a ventilator. In some embodiments, change in pressure data may be stored in a memory (e.g., storage 114) for use in later calculations.

At release operation 310, a plurality of volume amounts may be released from the patient circuit. The loss effect compensation module 118 may be configured to instruct the ventilator, during a ventilator self-test, to release a plurality of volume amounts from the closed ventilator circuit. In some embodiments, at least one component of the ventilator may release a plurality of volume amounts from the circuit during a delivery operation 304. For instance, during a self-test, a plurality of volume amounts may be released from the circuit prior to connection of the circuit to a patient. One or more ventilator components (e.g., inspiratory module 104) may receive instructions from loss compensation module 118 to release at least a portion of the total volume of gas in the circuit. According to embodiments, the ventilator may release an initial volume amount to the circuit. The initial volume amount and the subsequent plurality of volume amounts may be released from the circuit prior to connection of the circuit to a patient (e.g., patient 150). According to embodiments, the plurality of released volume amounts may be predetermined by the ventilator based on the configuration of the ventilator or determined by the ventilator based on ventilator and/or patient parameters or settings. In an alternative embodiment, the initial volume release amount may be input or selected by an operator. For instance, according to embodiments, an initial volume amount release value is received via input or selection by an operator, e.g., via a graphical user interface, keyboard, mouse, and/or any other suitable input device for receiving and interpreting operator commands, instructions, and/or selections. In an alternative embodiment, the desired released volume is determined by the ventilator. Volume release during self-test may be repeated. During subsequent releases, the ventilator may repeatedly release a volume amount (e.g., substantially equal to the first delivered volume amount) into the closed circuit. The number of and spacing between volume releases may be pre-determined by the ventilator or by an operator. For instance, volume releases may occur over a specified time duration. Volume releases may also occur in substantially equal time increments.

At receive operation 312, one or more pressure measurements may be received. According to some embodiments, a pressure measurement for each volume release may be received. Subtracting an amount of volume to the closed or substantially closed circuit may generally result in a pressure decrease. However, each consecutively released volume amount, while substantially constant, may result in a slightly different pressure decrease (e.g., each pressure decrease may be less than the previous pressure decrease). That is, additional volume releases may not release equal amounts of pressure on one or more ventilator components. Such pressure decreases within the tubing system may be measured by at least one component of the ventilator (e.g., sensor 107). A sensor may measure the tubing pressure based on the subtracted volume into the circuit. The tubing pressure may alternatively be measured by utilizing any known suitable methods or systems. A sensor may measure a pressure after each volume release. The sensor may be configured to measure a pressure amount at the patient wye or elsewhere in the circuit. The sensor may be any suitable sensing device as known by a person of skill in the art for a ventilator. The sensor may then transfer the pressure data to another component of the ventilator 100, such as controller 110, processor 116, and/or loss effect compensation module 118. In embodiments where the sensor transfers the pressure data to a component other than the loss effect compensation module 118, the loss effect compensation module 118 may receive the pressure information from the other component of the ventilator 100. Pressure data may be collected to derive applicable values for the parameters of the best fit to the data for the tubing configuration in use. Tubing pressure measurements may be sent to the loss effect compensation module 118 for further processing. Tubing pressure measurements may also be stored in a memory (e.g., storage 114).

At calculate operation 314, a change in pressure for each volume release may be calculated. For instance, during the change in pressure calculation operation 308, the loss effect compensation module 118 may calculate a relative change in pressure for each volume release. The change in tubing pressure may be based on the subtracted volume releasing from the tubing system after each volume delivery. In some embodiments, each subsequent volume release, pressure may be subtracted from a previous volume release pressure to calculate a change in pressure between the two volume releases. The change in tubing pressure may be calculated by utilizing any known suitable methods or systems. In alternative embodiments, method 300 may utilize a processor (e.g., processor 116) to calculate the change in tubing pressure, and transfer the change in pressure data to the loss effect compensation module 118. Processor may include any suitable processing device as known by a person of skill in the art for a ventilator. In some embodiments, change in pressure data may be stored in a memory (e.g., storage 114) for use in later calculations.

At fit operation 316, the calculated change in pressure data may be fitted to a non-linear model. For instance, one or more components of ventilator 100 (e.g., processor 116 or loss effect compensation module 118) may be configured to calculate a compliance value (after adding or releasing a certain volume, the circuit pressure increases or decreases, respectively; and compliance is defined as change in volume divided by change in pressure) via any suitable means. The calculated compliance data for volume delivery may be fitted to an inhalation non-linear model (compliance versus pressure rise) equation and the calculated compliance data for volume release may be fitted to an exhalation non-linear model (compliance versus pressure drop) equation. According to embodiments, compliance data may be plotted versus pressure (e.g., delivery simulation), or versus any other suitable parameter as may be useful to a clinician. According to embodiments, change in pressure data may be plotted such that each delivery instance may be independently identified. Or, a pressure-volume plot may be found useful.

At derive operations 318 and 320, a tubing compliance compensation model coefficients may be derived from the fitted curve. For instance, the loss effect compensation module 118 may derive inhalation and exhalation tubing compliance compensation model coefficients from respectively fitted non-linear curves. In one embodiment, an inhalation tubing compliance compensation model coefficients may be characterized by the following equation:

$$C_i = c_1 \ln(\Delta P) + c_2$$

Where $C_i$=tubing compliance for volume contraction, $c_1$ and $c_2$ are constant model coefficients derived during an inhalation simulation, and $\Delta P = P_{iend} - P_{eend}$.

In another embodiment, an inhalation tubing compliance may be characterized by the following equation:

$$C_i = c_1(\Delta P)^{c_2}$$

Where $C_i$=tubing compliance for volume contraction, $c_1$ and $c_2$ are constant model coefficients derived during an inhalation simulation, and $\Delta P = P_{iend} - P_{eend}$.

Similar model equations may be derived from the fitted curve to estimate an exhalation tubing compliance for gas volume expansion compliance. For instance, an exhalation tubing compliance may be characterized by the following equation:

$$C_e = c_1 \ln(\Delta P) + c_2$$

Where $C_e$=tubing compliance for volume expansion, $c_1$ and $c_2$ are constant model coefficients derived during an exhalation simulation, and $\Delta P = P_{iend} - P_{eend}$.

In another embodiment, an exhalation tubing compliance may be characterized by the following equation:

$$C_e c_1(\Delta P)^{c_2}$$

Where $C_e$=tubing compliance for volume expansion, $c_1$ and $c_2$ are constant model coefficients derived during an exhalation simulation, and $\Delta P = P_{iend} - P_{eend}$.

Tubing compliance compensation model coefficients for a circuit may be saved in a memory (e.g., storage 114) to be utilized during ventilation with that particular circuit. The model equation for estimating a tubing compliance compensation coefficients may be any suitable model providing a reasonably accurate prediction of the tubing compliance based on ventilator settings, pressure measurements, available hardware characteristics, and/or patient type. Provisions may be made to include updates to the model based on respiratory mechanics parameters extracted from ventilator data during patient treatment. Selection of a model may be optimized on a regressive basis (e.g., loss effect compensation module 118 may select the model that returns the highest $R^2$ value). The model equations described above are non-limiting examples of how an estimate may be obtained based on the measured volume and pressure values. A tubing compliance compensation model coefficients may be estimated during a self-test whenever a tubing system is modified (e.g., a tube of tubing system 130 is replaced, or tubing system 130 is replaced in its entirety).

Tubing compliance compensation volumes may then be estimated during patient ventilation. For instance, the loss effect compensation module 118 may then estimate a tubing compliance volume of the circuit (e.g., the amount of volume that may remain in ventilation tubing system 130 after volume delivery for inhalation and/or exhalation). For instance, the loss effect compensation module 118 may utilize the tubing compliance compensation coefficients in a loss effect compliance volume equation to estimate a tubing compliance volume. The loss effect compliance volume equation may be utilized during patient ventilation to accurately compensate for loss effects due to tubing compliance.

For instance, tubing compliance volume may be estimated using the equation:

$$V_{comp} = C_{tubing} * (\Delta P)$$

Where $V_{comp}$=tubing compliance volume, $C_{tubing} = C_i$ or $C_e$, and $\Delta P = P_{iend} - P_{eend}$.

During an inhalation, an inhalation tubing compliance model coefficients may be used in the loss effect adjusted compliance volume equation to compensate for compressed volume during inhalation. For instance, to estimate tubing compliance for volume contraction, the equation may be:

$$V_{comp} = C_i * (\Delta P)$$

Where $C_i = c_1(\Delta P)^{c_2}$, $c_1$ and $c_2$ are constants derived during an inhalation simulation, and $\Delta P = P_{iend} - P_{eend}$.

In contrast, during exhalation, an exhalation tubing compliance coefficient may be used in the loss effect adjusted compliance volume equation to compensate for volume remaining in the circuit during exhalation. For instance, to estimate tubing compliance during gas expansion, the equation may be:

$$V_{comp} = C_e * (\Delta P)$$

Where $C_e = c_1(\Delta P)^{c_2}$, $c_1$ and $c_2$ are constants derived during an exhalation simulation, and $\Delta P = P_{iend} - P_{eend}$.

It is further contemplated that the volume compensation equation may be any suitable model providing a reasonably accurate estimation of the tubing compliance based on ventilator settings, pressure measurements, available hardware characteristics, and/or patient respiratory mechanics parameters extracted from ventilator data. The model described above is a non-limiting example of how a tubing compliance volume estimate may be obtained based on a tubing compliance compensation model coefficients. It is further contemplated that more complex modeling strategies (building a bank of models to serve different ventilator settings and/or patient conditions) may also be utilized. Furthermore, parameters of such models may be dynamically updated and optimized during ventilation.

In some embodiments, after completing the ventilator setup and entering patient ventilation mode, method 300 may further provide an estimate for one or more respiratory or spirometry parameters. For instance, at least one component of the ventilator may estimate an inspiratory tidal volume or an exhaled tidal volume based on the derived tubing compliance compensation coefficients. According to embodiments, method 300 may provide a more accurate estimation of delivered tidal volume or exhaled tidal volume or respiratory mechanics parameters may be derived by using the pressure-based model including an estimate of tubing compliance during gas volume contraction $C_i$ (e.g., during inhalation) or an estimate of tubing compliance during gas volume expansion $C_e$ (e.g., during exhalation), as applicable, estimated via the embodiments described above in, for example, the Equation of Motion, or any other equation suitable for calculating delivered tidal volume or respiratory compliance or resistance. During ventilation, loss effect compensation module 118 may estimate a total volume delivery amount or an exhaled tidal volume. For instance, during an inhalation, loss effect compensation module 118 may estimate how much total volume to deliver to provide the desired tidal volume to the patient by adding an inhalation tubing compliance-compensated volume to the desired tidal volume. After an exhalation, a total exhaled volume may be measured and loss effect compensation module 118 may subtract the estimated exhalation tubing compliance-compensated volume from the total to determine how much volume was exhausted (e.g., an exhaled tidal volume) by the patient.

Alternatively, the loss effect compensation module 118 may allow the processor 116 or controller 110 to more accurately estimate inhaled and exhaled tidal volume and/or spirometry. For instance, the loss effect compensation module 118 may send the estimated tubing compliance volume to other components of the ventilator 100, such as the controller 110, processor 116, pneumatic system 102, and/or display 122 for use in calculating delivery (e.g., delivery of an inhaled tidal volume) and spirometry (e.g., measurement of an exhaled or inhaled tidal volume) parameters and compensating for tubing compliance volume during delivery and spirometry.

The ventilator may utilize any known methods for estimating tidal volume, including any equations discussed above. In some embodiments, the ventilator during a calculation operation may also estimate spirometry data. In some embodiments, the spirometry data calculation is based on the estimated exhaled tidal volume. The ventilator may utilize any known methods for calculating spirometry data. In further embodiments, tubing compliance volume may be utilized to more accurately estimate respiratory resistance during inhalation and exhalation. Respiratory resistance may be estimated via the embodiments described above in, for example, the Equation of Motion, or any other equation suitable for calculating respiratory resistance. In further embodiments, method 300 may provide an estimate of patient lung compliance by utilizing the estimated tubing compliance volume in any suitable equation for estimating patient lung compliance. As related to ventilation, lung compliance refers to the lung volume achieved for a given amount of delivered pressure ($C=\Delta V/\Delta P$). Thus, one or more components of the ventilator (e.g., processor 116) may be configured to utilize the estimated delivered volume, based on the tubing compliance compensation estimate, to estimate lung volume compliance.

As should be appreciated, the particular steps and methods described above with reference to FIG. 3 are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present methods.

In some embodiments, a microprocessor-based ventilator that accesses a computer-readable medium having computer-executable instructions for performing the method of ventilating a patient with a medical ventilator is disclosed. This method may include performing the steps disclosed in method 300 above and/or as illustrated in FIG. 3.

As should be appreciated, the particular steps and methods described herein are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present methods.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the claims.

What is claimed is:

1. A ventilator system comprising:
   a pressure generating system adapted to generate a volume of breathing gas;
   a ventilation tubing system including a patient interface for connecting the pressure generating system to a patient;
   at least one sensor operatively coupled to at least one of the pressure generating system and the ventilation tubing system;
   a ventilator self-test, the ventilator self-test configured to:
      consecutively deliver a plurality of substantially equal volume amounts into a closed ventilator circuit; and consecutively release a plurality of substantially equal volume amounts from the closed ventilator circuit;

a loss effect compensation module, the loss effect compensation module configured to:
receive a pressure measurement for each volume delivery and each volume release from the ventilator self-test;
calculate a change in pressure for each volume delivery and each volume release;
fit the calculated change in pressure data for each volume delivery and each volume release to an inhalation non-linear tubing compliance model equation and an exhalation non-linear tubing compliance model equation, respectively;
derive one or more inhalation tubing compliance compensation coefficients from the inhalation non-linear tubing compliance model equation; and
derive one or more exhalation tubing compliance compensation coefficients from the exhalation non-linear tubing compliance model equation; and a processor in communication with and controlling the pressure generating system, the at least one sensor, the ventilator self-test, and the loss effect compensation module.

2. The ventilator system of claim 1, wherein the loss effect compensation module is further configured to estimate an inhalation tubing compliance compensation volume by inputting the one or more inhalation tubing compliance compensation coefficients into a loss effect adjusted tubing compliance model.

3. The ventilator system of claim 2, wherein the loss effect compensation module is further configured to add the estimated inhalation tubing compliance volume amount to an inspiratory tidal volume amount and provide an instruction to deliver the combined amount to a patient through the ventilation tubing system.

4. The ventilator system of claim 1, wherein the loss effect compensation module is further configured to estimate an exhalation tubing compliance compensation volume by inputting the one or more exhalation tubing compliance compensation coefficients into a loss effect adjusted tubing compliance model.

5. The ventilator system of claim 4, wherein the loss effect compensation module is further configured to estimate an expiratory tidal volume of a patient by subtracting the exhalation tubing compliance compensation volume from a total expiratory volume.

6. The ventilator system of claim 1, wherein the loss effect compensation module is further configured to estimate a circuit resistance by estimating at least one circuit resistance parameter from an equation utilizing the one or more inhalation or exhalation tubing compliance compensation coefficients and utilizing the estimated circuit resistance parameter in an equation for estimating circuit resistance.

7. The ventilator system of claim 1, wherein the loss effect compensation module is further configured to estimate a patient lung compliance by estimating at least one patient lung compliance parameter from an equation utilizing the one or more inhalation or exhalation tubing compliance compensation coefficients and utilizing the estimated patient lung compliance parameter in an equation for estimating patient lung compliance.

8. The ventilator system of claim 1, wherein the loss effect compensation module is further configured to estimate a patient lung compliance by estimating at least one patient lung compliance parameter from an equation utilizing the one or more inhalation or exhalation tubing compliance compensation coefficients and utilizing the estimated patient lung compliance parameter in an equation for estimating patient lung compliance.

* * * * *